(12) United States Patent
Xu et al.

(10) Patent No.: US 9,501,823 B2
(45) Date of Patent: Nov. 22, 2016

(54) METHODS AND SYSTEMS FOR CHARACTERIZING ANGLE CLOSURE GLAUCOMA FOR RISK ASSESSMENT OR SCREENING

(71) Applicants: AGENCY FOR SCIENCE, TECHNOLOGY AND RESEARCH, Singapore (SG); SINGAPORE HEALTH SERVICES PTE LTD, Singapore (SG)

(72) Inventors: Yanwu Xu, Singapore (SG); Jiang Liu, Singapore (SG); Wing Kee Damon Wong, Singapore (SG); Beng Hai Lee, Singapore (SG); Tin Aung, Singapore (SG); Baskaran Mani, Singapore (SG); Shamira Perera, Singapore (SG)

(73) Assignees: Agency for Science, Technology and Research, Singapore (SG); Singapore Health Services Pte Ltd, Singapore (SG)

( * ) Notice: Subject to any disclaimer, the term of this patent is extended or adjusted under 35 U.S.C. 154(b) by 0 days.

(21) Appl. No.: 14/419,237

(22) PCT Filed: Aug. 1, 2013

(86) PCT No.: PCT/SG2013/000323
§ 371 (c)(1),
(2) Date: Feb. 2, 2015

(87) PCT Pub. No.: WO2014/021782
PCT Pub. Date: Feb. 6, 2014

(65) Prior Publication Data
US 2015/0161785 A1 Jun. 11, 2015

(30) Foreign Application Priority Data
Aug. 2, 2012 (SG) .................. 201205752

(51) Int. Cl.
*G06K 9/00* (2006.01)
*G06T 7/00* (2006.01)
(Continued)

(52) U.S. Cl.
CPC ............. *G06T 7/0012* (2013.01); *A61B 3/117* (2013.01); *G06K 9/46* (2013.01); *G06T 7/0042* (2013.01);
(Continued)

(58) Field of Classification Search
USPC ........ 382/100, 103, 106–107, 128–134, 140, 382/162, 168, 173, 181, 199, 203, 209, 224, 382/232, 254–257, 276, 190; 378/21; 604/8, 294; 623/6.14
See application file for complete search history.

(56) References Cited

U.S. PATENT DOCUMENTS 7,186,232 B1 * 3/2007 Smedley ............. A61F 9/00781
604/294
8,506,515 B2 * 8/2013 Burns ................. A61F 9/00781
604/8

(Continued)

OTHER PUBLICATIONS

Jun Cheng, et al., "Focal Biologically Inspired Feature for Glaucoma Type Classification", MICCAI 2011, Part III, LNCS 6893, pp. 91-98, (2011).*

(Continued)

*Primary Examiner* — Seyed Azarian
(74) *Attorney, Agent, or Firm* — Blakely, Sokoloff, Taylor & Zafman LLP

(57) ABSTRACT

A method is proposed for analyzing an optical coherence tomography (OCT) image of the anterior segment (AS) of a subject's eye. A region of interest is defined which is a region of the image containing the junction of the cornea and iris, and an estimated position the junction within the region of interest is derived. Using this a second region of the image is obtained, which is a part of the image containing the estimated position of the junction. Features of the second region are obtained, and those features are input to an adaptive model to generate data characterizing the junction.

11 Claims, 6 Drawing Sheets

(51) Int. Cl.
  A61B 3/117   (2006.01)
  G06K 9/46    (2006.01)
  A61M 35/00   (2006.01)
  A61B 3/10    (2006.01)

(52) U.S. Cl.
  CPC ....... *A61B 3/102* (2013.01); *G06K 2009/4666* (2013.01); *G06T 2207/10072* (2013.01); *G06T 2207/10101* (2013.01); *G06T 2207/30041* (2013.01)

(56) References Cited

U.S. PATENT DOCUMENTS

| | | | | |
|---|---|---|---|---|
| 2007/0276315 | A1* | 11/2007 | Haffner | A61F 9/00781 604/8 |
| 2011/0190657 | A1 | 8/2011 | Zhou et al. | |
| 2013/0310930 | A1* | 11/2013 | Tu | A61F 9/00781 623/6.14 |

OTHER PUBLICATIONS

Jing Tian, et al., "Automatic Anterior Chamber Angle Assessment for HD-OCT Images", IEEE Transactions on Biomedical Engineering, vol. 58, No. 11, pp. 3242-3249, (Nov. 2011).*

PCT Notification of Transmittal of the International Search Report and the Written Opinion of the International Searching Authority, or the Declaration for PCT Counterpart Application No. PCT/SG2013/000323, 10 pp., (Oct. 22, 2013).

Alain Coron, et al., "Automatic Segmentation of the Anterior Chamber in in vivo High-frequency Ultrasound Images of the Eye", 2007 IEEE Ultrasonics Symposium, pp. 1266-1269, (2007).

Jorg Meier, et al., "Effects of Preprocessing Eye Fundus Images on Appearance Based Glaucoma Classification", Proceedings of the 12th International Conference on Computer Analysis of Images and Patterns (CAIP 2007), pp. 165-172, (Aug. 27, 2007).

Lijun Cheng, et al., "SVM and Statistical Technique Method Applying in Primary Open Angle Glaucoma Diagnosis", Proceedings of the 8$^{th}$ World Congress on Intelligent Control and Automation, Jinan, China, pp. 2973-2978, (Jul. 6-9, 2010).

Navneet Dalal, et al., "Histograms of Oriented Gradients for Human Detection", IEEE Computer Society Conference on Computer Vision and Pattern Recognition (CVPR 2005), vol. 1, pp. 886-893, (2005).

Jun Cheng, et al., "Focal Biologically Inspired Feature for Glaucoma Type Classification", MICCAI 2011, Part III, LNCS 6893, pp. 91-98, (2011).

Mehrdad J. Gangeh, et al., "A Texton-Based Approach for the Classification of Lung Parenchyma in CT Images", MICCAI 2010, Part III, LNCS 6363, pp. 595-602, (2010).

Jing Tian, et al., "Automatic Anterior Chamber Angle Assessment for HD-OCT Images", IEEE Transactions on Biomedical Engineering, vol. 58, No. 11, pp. 3242-3249, (Nov. 2011).

Tian Jing, et al., "Automatic Detection of Schwalbe's Line in the Anterior Chamber Angle of the Eye using HD-OCT Images", 32nd Annual International Conference of the IEEE EMBS, Buenos Aires, Argentina, pp. 3013-3016, (Aug. 31-Sep. 4, 2010).

Sunita Radhakrishnan, et al., "Reproducibility of Anterior Chamber Angle Measurements Obtained with Anterior Segment Optical Coherence Tomography", Investigative Ophthalmology & Visual Science, vol. 48, No. 8, pp. 3683-3688, (Aug. 2007).

Wei Wu, et al., "A Compound Segmentation Algorithm for Anterior Chamber Angle in OCT Image", 4$^{th}$ International Conference on Biomedical Engineering and Informatics (BMEI), pp. 12-15, (2011).

Yanwu Xu, et al., "Automated Anterior Chamber Angle Localization and Glaucoma Type Classification in OCT Images", 35$^{th}$ Annual International Conference of the IEEE Engineering in Medicine and Biology Society (EMBC), pp. 7380-7383, (Jul. 3, 2013).

* cited by examiner

METHODS AND SYSTEMS FOR CHARACTERIZING ANGLE CLOSURE GLAUCOMA FOR RISK ASSESSMENT OR SCREENING

CROSS-REFERENCE TO RELATED APPLICATIONS

This patent application is a U.S. National Phase Application under 35 U.S.C. §371 of International Application No. PCT/SG2013/000323, filed Aug. 1, 2013, entitled METHODS AND SYSTEMS FOR CHARACTERIZING ANGLE CLOSURE GLAUCOMA FOR RISK ASSESSMENT OR SCREENING, which claims priority to Singapore Patent Application No. 201205752-7, filed Aug. 2, 2012.

FIELD OF THE INVENTION

The present invention relates to automatic methods for analysing at least one image of a portion of the eye comprising the junction of the cornea and iris. More particularly, it relates to a method for extracting from the image data which may be indicative of the presence of primary angle closure glaucoma (PACG). It further relates to computer systems for performing the methods.

BACKGROUND OF THE INVENTION

Glaucoma is classified into "open angle glaucoma" and "closed angle glaucoma" according to the angle at the junction between the cornea and iris. This junction is mainly responsible for drainage of aqueous humor. The angle is referred to as the anterior chamber angle (ACA). A first step of the process to measure it is to locate the anterior chamber angle region ("angle region") in an image including the junction, so that classification and measurement can be done. The step of locating the angle region ("angle region segmentation") is conventionally performed manually, but this is tedious and subject to human error. Techniques have been proposed to do it automatically using edge detection algorithms, but the edge detection step is susceptible to noise in the image. It would therefore be desirable to provide automatic methods for angle region segmentation which are robust to noise. It would further be desirable to provide a process which is capable of generating data indicative of PACG automatically given only a single image of the junction.

SUMMARY OF THE INVENTION

The present invention aims to provide a new and useful method and computer system for analysing an image of the junction between a cornea and an iris, to obtain data characterizing the junction.

In general terms, the present invention proposes: defining a region of interest which is a region of the image containing the junction; estimating the position of the junction within the region of interest; defining a second region of the image as a part of the image containing the estimated position of the junction; deriving features of the second region; and inputting those features to an adaptive model.

The process for estimating the position of the junction includes binarizing the region of interest, seeking a connected component of the region of binarized region of interest which best fits pre-known biological knowledge describing a low-intensity portion of the ROI including the junction, and then estimating the position of the junction as a corner of the connected region. The biological knowledge relates to the size and position of the low-intensity portion of the ROI.

The low-intensity portion of the ROI can take several forms, and methods are presented for modifying the binarized image to eliminate irrelevant portions of the low-intensity portion of the ROI.

In accordance with an embodiment of the present invention, the method examines the whole angle region, to derive high-dimensional visual features (e.g. with at least 10, at least 100 or at least 1000 numerical values), and an adaptive model trained by a learning algorithm is used to classify an anterior chamber angle as open or closed. A preferred embodiment of the present invention comprises a system that acquires PACG-related features, measures, analyses and performs data mining on such acquired data and provide helpful information that may provide further understanding of the eye disease.

We have determined experimentally that certain embodiments of the invention give successful results without needing high definition images. They are robust to noise and computationally efficient enough for practical applications.

Preferred embodiments of the invention are fully automatic (the term "automatic" is used in this document to describe performing a method substantially without human involvement, save perhaps for initiating the method). They do not need manual input such as ROI labelling, and employ automatically derivable visual features rather than clinical features.

The invention may be defined as a method, as a computer programmed to perform the method, or as the software operative when run by the computer to perform the method. The method may include further steps of testing a patient to identify a medical condition. It may further include steps of treating a patient who has been identified as having the medical condition.

BRIEF DESCRIPTION OF THE FIGURES

An embodiment of the invention will now be described for the sake of example only with reference to the following figures, in which.

DETAILED DESCRIPTION OF THE EMBODIMENT

Figure 1:
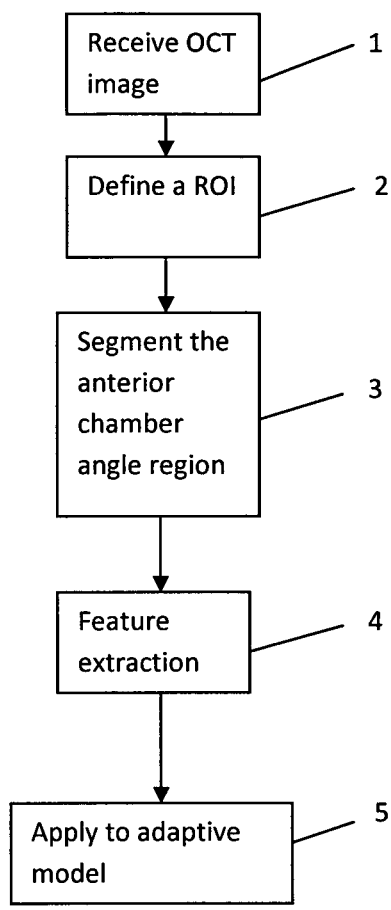
FIG. 1 is a flow diagram of a method which is an embodiment of the invention.

FIG. 1 below illustrates a schematic diagram of a method which is an embodiment of the present invention.

In a first step 1 at least one optical coherence tomography (OCT) image of the anterior segment (AS) of the eye (in short, an "AS-OCT image") is received. This is a greyscale image. The goal of the next steps of the method is to segment a clear ACA region aligned with its vertex from the input AS-OCT image.

In step 2 a region of interest is defined within the image. In step 3, an anterior chamber angle region of the image is derived, which is a portion of the image believed to include the anterior chamber angle, i.e. the junction between the cornea and the iris. In step 4 one or more features of the anterior chamber angle region are derived. In step 5, the features are applied (input) to an adaptive model which has been trained to output at least one variable characterizing the junction.

Figure 2:
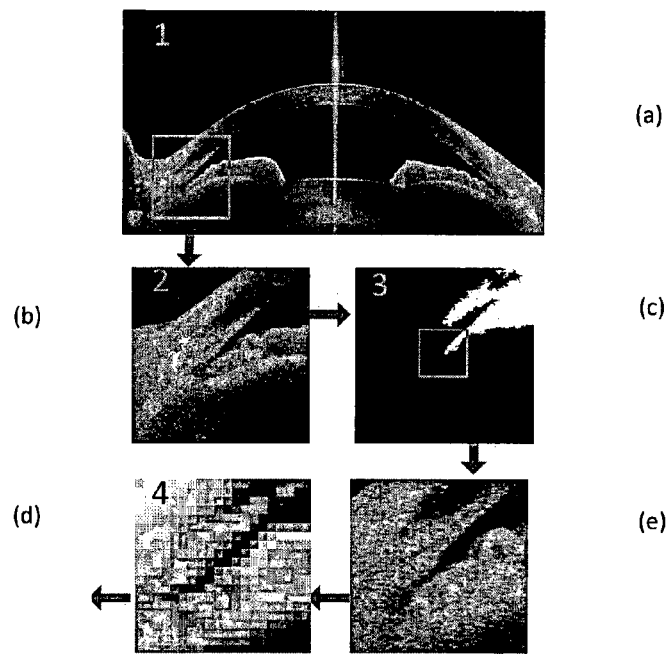
FIG. 2, which is composed of FIGS. 2(a) to 2(e), shows schematically the application of the method of FIG. 1 to an image.

FIG. 2 shows the performance of these steps on an AS-OCT image shown in FIG. 2(*a*). Step 1 is performed by cropping the input image (which may for example have 1668×900 pixels). Specifically predefined portion of the input image is defined as the ROI, which may for example have 400×400 pixels. This image is shown as a square on FIG. 2(*a*), and it is shown in an expanded view in FIG. 2(*b*).

Figure 4:
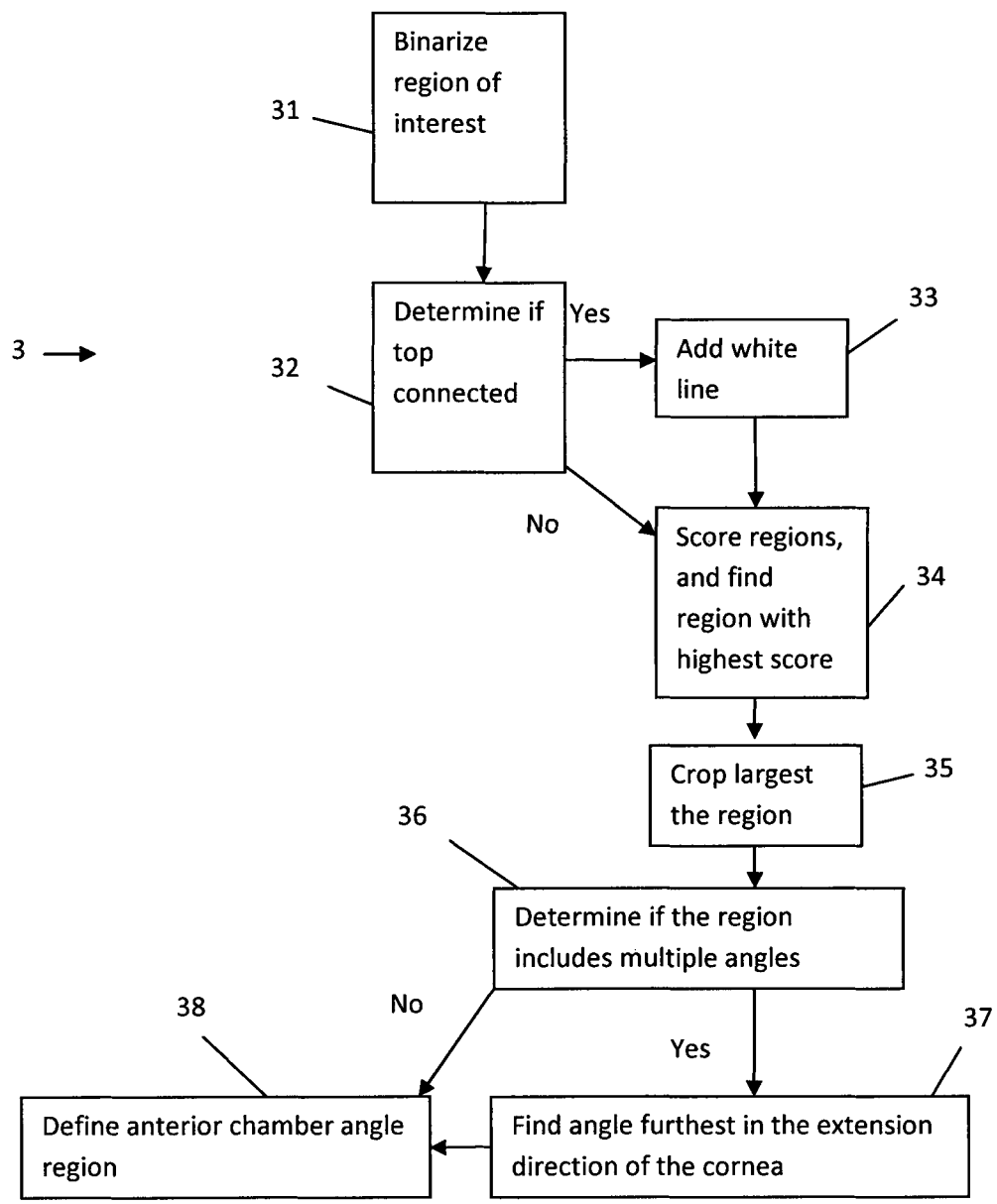
FIG. 4 is a more detailed flow-diagram of one of the steps of the method of FIG. 1.

The next task (step 3) is to segment the anterior chamber angle region by employing and adapting a widely used segmentation algorithm: the connected component labelling segmentation method. The process is illustrated in FIG. 4.

In a first sub-step 31, the ROI is converted to a binary image (e.g. with each pixel being either set to "black" (i.e. with value 0), or "white" (i.e. with intensity 1)) by thresholding. This produces the image of FIG. 2(*c*) in which the anterior chamber angle region is part of the black region (i.e. low-intensity portion of the ROI) located at the top right of the ROI. The thresholding is done using a small valued threshold to preserve more details of the angle. Using a larger threshold (e.g. one derived adaptively) will lose details of the extreme end part of the angle. A morphological operation is performed to remove isolated noise points.

Figure 3:
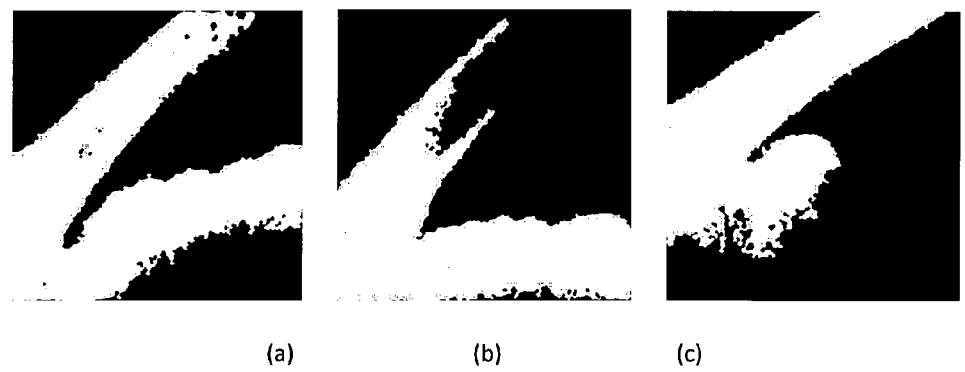
FIG. 3, which is composed of FIGS. 3(a) to 3(c), shows three types of images resulting from a binarization sub-step of the method of FIG. 1.

The present inventors have observed that the binary images obtained as explained above can be categorized in to 3 profiles (exemplified by images FIG. 3(*a*) to (*c*)). For the first profile (FIG. 3(*a*)), the ACA region is clearly separated from other black region(s), which makes the image very easy to process. Thus, it would be desirable to convert the other two profiles into this profile.

For the second profile (FIG. 3(*b*)), the ACA region is connected with the top-left black region. In sub-step 32 the method determines if this the case by finding out whether the sum of the intensities of the top row of pixels is 0. If so, in sub-step 33, the embodiment searches for the top-most white point, and then adds a vertical white line from this point to the upper boundary in order to segment the ACA region from the top-left black region.

For the last profile (FIG. 3(*c*)), the bottom part of the ACA region is connected with another black region. This arises because the iris is not fully captured during the imaging process. The embodiment deals with this case in a post processing step explained below. The embodiment may test whether this case has arisen by testing whether the sum of the pixel intensities in bottom-left 40×40 region of the binarized image is less than 800.

In sub-step 34, the binarized image (to which, as mentioned above, a white line has been added in sub-step 33 in the case that the top row of pixels are all black) is processed to identify and label the black regions. The ACA region can be selected from the set of identified black regions using a weight method. Specifically, for each black region, we compute its pixel number N and center coordinate (Cx, Cy), and use these to produce a corresponding weight Nw of each region, which is defined as:

$$Nw = \begin{cases} 25N, & Cx \geq 200, Cy < 200 \\ 5N, & Cx < 200, Cy < 200 \\ 5N, & Cx \geq 200, 200 \leq Cy < 300 \\ N, & Cx < 200, 200 \leq Cy < 300 \\ 0, & Cy \geq 300 \end{cases}$$

Figure 5:
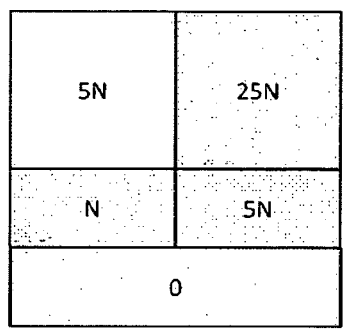
FIG. 5 illustrates a process for assigning a score to each of a number of connected regions of a binarized region of interest in the method of FIG. 1.

This is illustrated in FIG. 5, in which the outer line is the area of the ROI. FIG. 5 shows the weight Nw which is generated for each possible location of the center coordinate (Cx, Cy). The black region which has the largest Nw value is selected as the candidate ACA region.

Figure 6:
FIG. 6, which is composed of FIGS. 6(a) and 6(b), illustrates sub-steps of the process of FIG. 4.

In sub-step 35 a post processing procedure is applied to deal with the case illustrated in FIG. 3(*c*). FIG. 6(*a*) shows a possible such image. In contrast to the binarized images explained above, in FIG. 6(*a*) the candidate ACA region is illustrated in white (i.e. intensity 1). The embodiment first finds out the top-most white point of each column, then computes the difference between each pair of nearest-neighbour columns, and then finds the left-most column for which the top-most white point is at least 30 (pixels) higher than its next-neighbouring column to the left. The top-most white point of the former column is taken as a reference point of the ACA. After that, we crop out the region from the reference point to the right bottom, count the white pixel numbers of each row, and then find out the top-most row which has the smallest number of white pixels, and label it as the reference row; finally we give a zero value to all pixels below this reference row, giving the result of FIG. 6(*b*).

Figure 7:
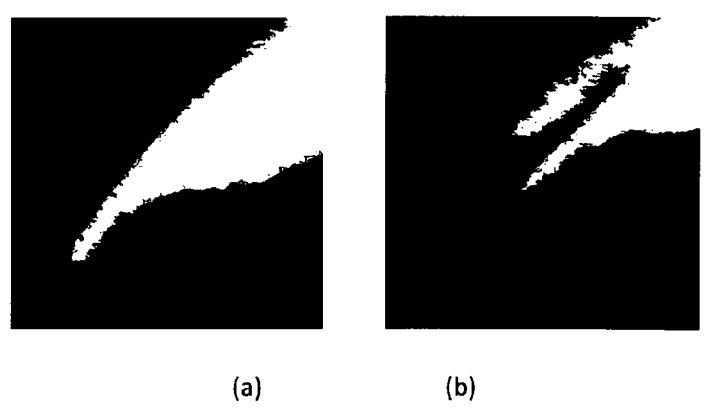
FIG. 7, which is composed of FIGS. 7(a) and 7(b), illustrates two sorts of images produced using the process of FIG. 4.

We have observed that the process produces end results with one of two 2 profiles, illustrated in FIGS. 7(*a*) and 7(*b*), where the ACA region is illustrated as white (i.e. intensity 1). The embodiment tests which of these two cases, has arisen by determining the number of angles in sub-step 36.

Figure 8:
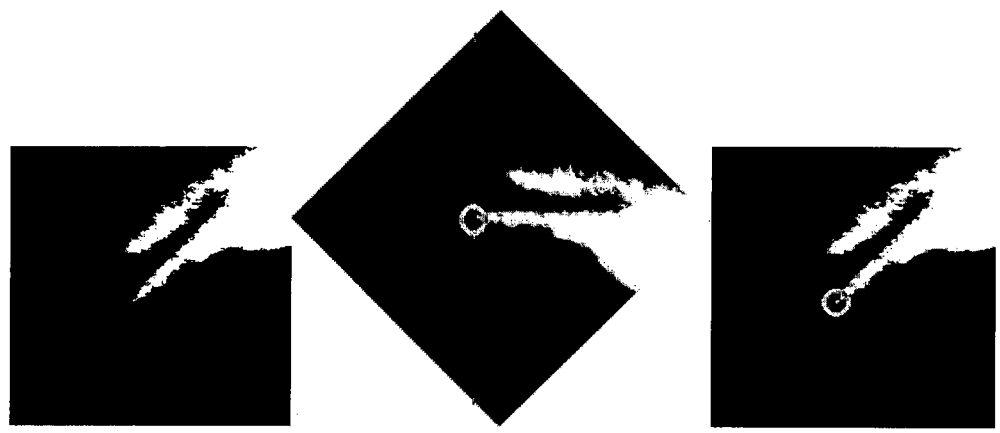
FIG. 8 illustrates a process performed by the embodiment in the case that the process of FIG. 4 results in an image of the sort shown in FIG. 7(b)

For the first case (FIG. 7(*a*)), there is a single angle, and the junction is identified as a vertex which is the bottom-left white point. For the second case (with multiple angles, as shown in FIG. 7(*b*)), in sub-step 37 the embodiment rotates the image by 45 degrees clockwise, derives the vertex as the left-most white point (i.e. the one which is furthermost in the extension direction of the connected region towards the junction). If there are several points which are furthest to the left, the embodiment selects the bottom-most one as the vertex, and calculates its original position on the non-rotated image. The whole process is illustrated in FIG. 8. In the second and third images of FIG. 8 the vertex is illustrated as a circle. In fact, sub-step 37 may be performed even if there is only a single angle.

Once the vertex is obtained from each ACA region, a 200×200 region in the original image around the vertex is cropped (i.e. a second region of the image), and this is used as the region for ACA analysis (classification). We have determined experimentally that the method above generates a second region including the anterior chamber angle with a very high probability.

Each ACA region is thus represented by a 200×200 image which is a second region of the original image. The 200×200 image may be expressed in several ways to extract visual features: as a gray scale image, a binary image and/or other images, such as a representation of the edges of the ACA. Many numerical features (i.e. values) can be obtained from the second region of the image using existing numerical methods (for example using pattern recognition methods). Suitable methods include the HOG method (see N. Dalai and B. Triggs, "Histograms of oriented gradients for human detection" in CVPR, 2005, vol. 1, pp. 1886-93), the BIF method (J. Cheng, D. Tao, J. Liu, D. W. K. Wong, B. H. Lee, M. Baskaran, T. Y. Wong and T. Aung, "Focal biologically inspired feature for glaucoma type classification", in MICCAI, 2011, vol. 6893, pp. 91-8) and the HEP (histogram equalized pixel) method (see below). The numerical features represent visual features of the image, rather than clinical features. The embodiment uses them for classifying the image. The classification process is performed by inputting the features to an adaptive model, which was produced by a supervised learning process based on example images ("training set") associated with corresponding classification values.

In a first experimental implementation of the invention, the embodiment transformed each original image into a 40000-dimensional feature vector. We trained an RBF-based non-linear SVM classifier for classification based on this feature vector. The training was done using a set of example images for each of which the ACA had been manually classified as either open or closed by three ophthalmologists. Once the SVM was trained, the SVM was very accurate in classifying additional images.

In an improved experimental implementation, we use the histogram equalized pixel (HEP) values as a feature that is effective and computationally efficient. This is motivated by the intensity of a pixel being a natural feature (see M. J. Gangeh, L. Sørensen, S. B. Shaker, M. S. Kamel, M. de Bruijne, and M. Loog, "A texton-based approach for the classification of lung parenchyma in ct images," in MICCAI, 2010, vol. 6363, pp. 595-602) to classify whether it is on a closed angle. However, using all the pixels in the n×n region will generate features that are too high dimensional and may also introduce too much noise. Therefore, we downsampled the image to reduce the feature dimension. The additional quantization with fewer bins before downsampling enhances the contrast between pixels and provides more distinguishable features.

Figure 9:
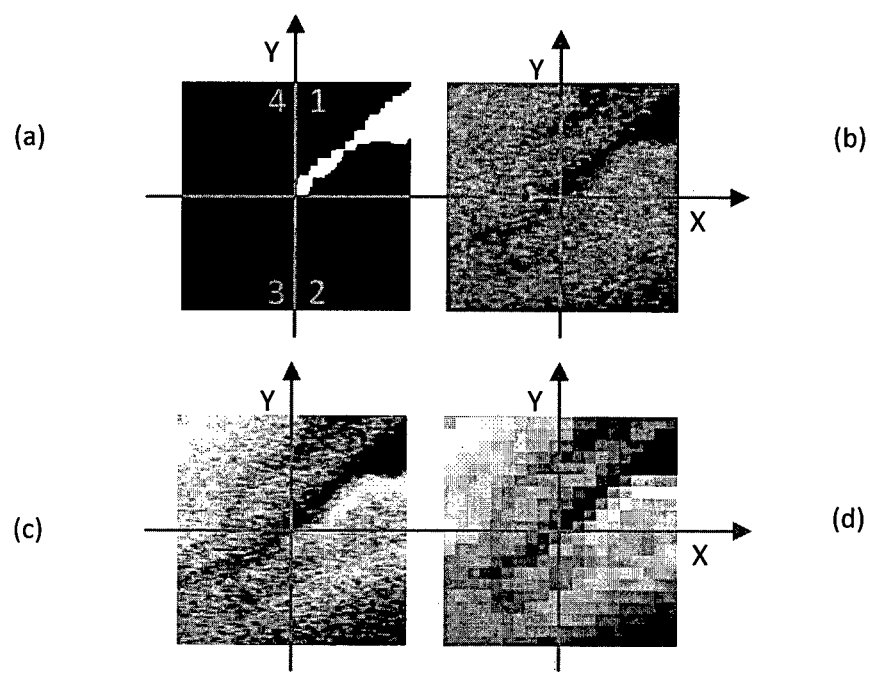
FIG. 9 is composed of FIGS. 9(a) to 9(d) which respectively illustrate four ACA feature representations used in an implementation of the embodiment, namely binary, grayscale, histogram equalized and HEP.

As illustrated in FIG. 9, the n×n grayscale image of ACA is first enhanced by quantizing to 8 bins (histogram equalization, as shown in FIG. 9(c)), and then downsampling to d×d (d<n) to produce an image which is shown in FIG. 9(d). The downsampled image is then vectorized (i.e. transformed from a 2D matrix to a vector) to produce a vectored image f which is the HEP feature. For efficiency, a simple linear SVM classifier is employed, with a weight vector w trained to estimate the class label y (+1 for AC and −1 for OA) of a given feature vector f, according to $y = w^T f$. In experiments, a LIBLINEAR toolbox was used to train the SVM models. This was implemented with Matlab and tested on a four-core 3.4 GHz PC with 12 GB RAM. A total of 2048 images are used for the experiments. The images are from 8 circular scan videos of 8 patient eyes with glaucoma, 4 of them with PACG and other 4 with primary open angle glaucoma (POAG). Each video contains 128 frames, and each frame is split into 2 images since it contains two angles and the right angle image is flipped horizontally.

The experiments are based on each single image, which is labelled as AC or OA by three ophthalmologists from a hospital. The classification evaluation followed the widely used leave-one-out (LOO) method, i.e., for each testing round, 512 images from one PACG and one POAG patients are used for testing while others are used for training, thus 16 rounds are performed to test all cases. The performance was assessed using a balanced accuracy with a fixed 85% specificity and area under ROC curve (AUC) which evaluates the overall performance. The balanced accuracy ($\bar{P}$), sensitivity (P+) and specificity (P−) are defined as:

$$\bar{P} = \frac{P_+ + P_-}{2}, \quad (1)$$
$$P_+ = \frac{TP}{TP + FN},$$
$$P_- = \frac{TN}{TN + FP}$$

where TP and TN denote the number of true positives and negatives, respectively, and FP and FN denote the number of false positives and negatives, respectively.

A comparison was performed of classification methods with several visual features (i.e., BIF, HOG and HEP) with different ACA region sizes (n=100, 150, 200) and two clinical features (angle opening distance, AOD, discussed in J. Tian, P. Marziliano, M. Baskaran, H. T. Wong, and T. Aung, "Automatic anterior chamber angle assessment for hd-oct images," IEEE Transactions on Biomedical Engineering, vol. 58, no. 11, pp. 3242-9, 2011; and Schwalbe's line bounded area, SLBA, discussed in J. Tian, P. Marziliano, and H. T. Wong, "Automatic detection of schwalbe's line in the anterior chamber angle of the eye using hd-oct images," in EMBC, 2010, pp. 3013-6). For the HEP feature extraction, d is set to 20 for efficiency reasons. For HOG and BIF feature extraction, the ACA is divided into 5×5 cells; 2×2 cells form a block for HOG, and 22 feature maps are used for BIF. It was found that:
1) Using HEP features with n=150 gave an AUC value of 0.921±0.036, and 84.0%±5.7% balanced accuracy ($\bar{P}$) at a 85% specificity (P−), while only requiring 0.26 s per image.
2) The visual feature based methods outperformed the clinical feature based ones, demonstrating that high dimensional visual features provide more information for classification and thus leading to higher performance. In addition, the performance dropped significantly in some videos that contained a lot of intermediate cases which are difficult to classify even for human experts.
3) Among visual feature based methods, the simplest HEP features outperformed HOG and BIF features. A possible explanation is that HOG features introduce noise and BIF is not very suitable for grayscale images.
4) Comparing methods based on the HEP feature with different ACA size n, the results are relatively stable, and the largest AUC is obtained when setting n=150, which was found to be not too small to lose useful information nor too big to introduce too much noises.

We also observed that histogram equalization can lead to about 2-3% relative improvement of AUC compared to downsampling only. In terms of processing speed, each ACA represented by a 400-dimension feature costs about 0.06 s for feature extraction and classification with a Matlab implementation, which can be further accelerated with a C++ implementation.

Figure 10:
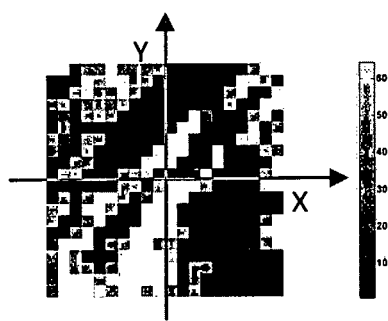
FIG. 10 shows a learned average weight matrix in the implementation.

In addition, we found a way to further reduce the feature dimension without significant reduction of accuracy. As shown in FIG. 9, with the proposed ACA localization, each ACA is aligned with its vertex at the center, and then the exact ACA should fall into quadrant 1; however, some ACAs are misaligned since the exact vertex of an ACA is very hard to distinguish when that region is blurred. In this case, the extreme ends of some ACA corners fall into quadrant 3, especially for closed ones. Thus we suppose that quadrant 1 and 3 may provide sufficient information for classification, which is supported by experiments. The average weight vectors $\bar{\omega}$ we obtained in the testing are illustrated in FIG. 10; for each dimension (shown as a block), a higher weight corresponds to a lighter color. One can observe that most of the dimensions with highest weights (in white) are in quadrant 1 and 3, as expected. Thus the performance of using all of the d×d pixels was compared with only using pixels in quadrants 1 and 3, the AUC reduction is less than 0.3% with a half dimension reduction.

What is claimed is:

1. A method for performance by a computer, for automatically processing an image including the junction between a cornea and an iris, the method comprising:
    defining a region of interest (ROI) in the image;
    deriving an estimated position of said junction within the region of interest;
    defining a second region of the image based on the estimated position of the junction;
    extracting features of the second region of the image; and
    inputting the extracted features to an adaptive model, the adaptive model outputting at least one variable characterizing the junction;
    wherein the estimated position of the junction is found by:
        binarizing the ROI,
        selecting a connected region of the binarized region of interest by a criterion which selects a connected region which has said junction as one of its corners, and
        deriving the estimated position of the junction from the connected region; and
    wherein the connected region is selected by:
        calculating a plurality of pixel numbers N and a plurality of center coordinates (Cx, Cy) of a plurality of connected regions of the binarized ROI,
        for each of the connected regions calculating a corresponding weight Nw from the plurality of pixel numbers and the plurality of center coordinates, and
        selecting the one of the connected regions of the ROI with the highest value of the weight Nw.

2. The method according to claim 1 further comprising generating the adaptive model by a supervised learning process.

3. The method according to claim 1 in which the image is an Optical Coherence Tomography (OCT) image.

4. The method according to claim 1 having a further operation of modifying the connected regions to remove extraneous portions.

5. The method according to claim 1 further comprising determining if the connected region contains multiple angles which are candidates to be the junction, and if the determination is positive selecting one which is furthest in an extension direction of the connected region.

6. The method according to claim 1 in which the adaptive model is a support vector machine trained to classify an anterior chamber angle (ACA) at said junction.

7. The method according to claim 6 in which the SVM is further configured to output a value indicative of whether the ACA is "open" or "closed".

8. A method for performance by a computer, for automatically processing an image including the junction between a cornea and an iris, the method comprising:
    defining a region of interest (ROI) in the image;
    deriving an estimated position of said junction within the region of interest;
    defining a second region of the image based on the estimated position of the junction;
    extracting features of the second region of the image; and
    inputting the extracted features to an adaptive model, the adaptive model outputting at least one variable characterizing the junction;
    wherein extracting features of the second region of the image comprises quantizing the intensity values of pixels of the second region of the image into a plurality of bins, the number of bins being less than the number of possible intensity values taken by pixels of the image.

9. A method for performance by a computer, for automatically processing an image including the junction between a cornea and an iris, the method comprising:
    defining a region of interest (ROI) in the image;
    deriving an estimated position of said junction within the region of interest;
    defining a second region of the image based on the estimated position of the junction;
    extracting features of the second region of the image; and
    inputting the extracted features to an adaptive model, the adaptive model outputting at least one variable characterizing the junction;
    wherein extracting features of the second region of the image comprises downsampling the image to generate a downsampled image comprising fewer pixels than the number of pixels in the second region of the image.

10. The method according to claim 9 in which the extracted features comprise at least some of the components of the downsized image.

11. The method according to claim 10 in which at least some components of the downsized image are not used as extracted features.

* * * * *